United States Patent
Donhowe (10) Patent No.: US 8,578,810 B2
(45) Date of Patent: Nov. 12, 2013

(54) JOINTED LINK STRUCTURES EXHIBITING PREFERENTIAL BENDING, AND RELATED METHODS

(75) Inventor: Caitlin Q. Donhowe, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 277 days.

(21) Appl. No.: 13/027,221

(22) Filed: Feb. 14, 2011

(65) Prior Publication Data

US 2012/0209253 A1    Aug. 16, 2012

(51) Int. Cl.
| | |
|---|---|
| B25J 17/00 | (2006.01) |
| B25J 17/02 | (2006.01) |
| B25J 18/00 | (2006.01) |
| A61B 1/00 | (2006.01) |

(52) U.S. Cl.
USPC ............. 74/490.04; 600/141; 901/21; 901/28

(58) Field of Classification Search
USPC ........... 74/490.01–490.07, 502.6; 901/12, 15, 901/27, 29; 600/139–142; 606/1, 130
See application file for complete search history.

(56) References Cited

U.S. PATENT DOCUMENTS

| | | | |
|---|---|---|---|
| 2,421,279 A | 5/1947 | Marty | |
| 3,132,911 A | 5/1964 | Heidler | |
| 4,393,728 A | 7/1983 | Larson et al. | |
| 4,494,417 A * | 1/1985 | Larson et al. | ................... 74/469 |
| 4,700,693 A * | 10/1987 | Lia et al. | ........................ 600/141 |
| 6,364,828 B1 * | 4/2002 | Yeung et al. | ................... 600/142 |
| 6,817,974 B2 | 11/2004 | Cooper et al. | |
| 7,250,027 B2 * | 7/2007 | Barry | .............................. 600/141 |
| 7,678,117 B2 | 3/2010 | Hinman et al. | |
| 7,828,808 B2 | 11/2010 | Hinman et al. | |
| 2003/0036748 A1 * | 2/2003 | Cooper et al. | ..................... 606/1 |
| 2005/0273084 A1 | 12/2005 | Hinman et al. | |
| 2005/0273085 A1 | 12/2005 | Hinman et al. | |
| 2006/0052664 A1 | 3/2006 | Julian et al. | |
| 2006/0178560 A1 * | 8/2006 | Saadat et al. | ................... 600/114 |
| 2008/0065102 A1 | 3/2008 | Cooper | |
| 2008/0214897 A1 * | 9/2008 | Matsuo | ......................... 600/139 |

(Continued)

FOREIGN PATENT DOCUMENTS

WO    WO2005120326 A2    12/2005

OTHER PUBLICATIONS

PCT/ US12/022736 International Search Report and Written Opinion of the International Searching Authority, mailed May 9, 2012, 9 pages.

(Continued)

*Primary Examiner* — David M Fenstermacher
*Assistant Examiner* — Jake Cook (57) ABSTRACT

In accordance with various exemplary embodiments of the present teachings, a surgical device can include a first pair of articulably coupled links, a second pair of articulably coupled links, and a tension member coupled to the first pair of links and the second pair of links such that altering tension in the tension member exerts a force tending to articulate the first pair of links and the second pair of links so as to bend the first pair of links and the second pair of links. The surgical device can be configured such that the first pair of links has a lower resistance to bending than the second pair of links upon altering the tension in the tension member.

12 Claims, 8 Drawing Sheets

(56) References Cited

U.S. PATENT DOCUMENTS

| | | |
|---|---|---|
| 2009/0024141 A1 | 1/2009 | Stahler et al. |
| 2010/0082041 A1 | 4/2010 | Prisco |
| 2010/0116080 A1 | 5/2010 | Pistor et al. |
| 2010/0116081 A1 | 5/2010 | Pistor et al. |
| 2010/0234831 A1 | 9/2010 | Hinman et al. |
| 2010/0249759 A1 | 9/2010 | Hinman et al. |
| 2010/0331820 A1 | 12/2010 | Prisco et al. |
| 2010/0331856 A1 | 12/2010 | Carlson et al. |
| 2010/0332030 A1 | 12/2010 | Larkin et al. |
| 2011/0152879 A1 | 6/2011 | Williams |

OTHER PUBLICATIONS

U.S. Appl. No. 12/780,417, filed May 14, 2010, entitled "Compliant Surgical Device."

U.S. Appl. No. 12/945,734, filed Nov. 12, 2010, entitled "Tension Control in Actuation of Multijoint Medical Instrument."

Vertut, Jean and Philippe Coiffet, *Teleoperation and Robotics: Evolution and Development*, English translation Prentice-Hall, Inc., Inglewood Cliffs, NJ, USA, 1986, 332 pages.

\* cited by examiner

JOINTED LINK STRUCTURES EXHIBITING PREFERENTIAL BENDING, AND RELATED METHODS

TECHNICAL FIELD

The present teachings relate to flexible, steerable instruments that include a series of links that articulate relative to each other via joints between adjacent links. In particular, the present teachings relate to such instruments used in performing various minimally invasive, including robotically-assisted, surgical procedures.

BACKGROUND

Kinematic chains are used in a variety of applications to provide elongate linkage structures. Examples of structures which employ such kinematic chains include, but are not limited to, robotically controlled instruments and/or minimally invasive surgical instruments. Minimally invasive surgical instruments can be either manually controlled or robotically controlled. Kinematic chains can include, as the entire chain or one or more parts thereof, structures analogous to the human skeleton and formed of a series of interconnected links (analogous to vertebrae). The links can be coupled to one another via joints to permit articulation of adjacent links relative to each other in one or more degrees of freedom (DOF). Through this articulation, these jointed link structures can likewise bend in one or more degrees of freedom (e.g., including pitch and/or yaw bending) to be placed in various curved shapes, analogous to a snake-like movement. Force transmission elements, such as, for example, tension members (e.g., cables, wires, and/or push rods) and/or compression members (e.g., push rods, Bowden cables), may interconnect the series of links to exert actuation forces that tend to articulate the links relative to one another to provide a desired overall bending and curved shape of the jointed linked structure.

Minimally invasive surgical techniques, whether performed manually or via robotically assisted systems, generally attempt to perform surgical procedures while minimizing damage to healthy tissue. One particular technique for achieving this goal employs surgical devices having bendable, steerable arms, wrists or the like that are formed of jointed link structures which are able to reach a target work site inside a patient by at least partially following a natural lumen, such as, for example, the digestive tract, blood-carrying lumens, bronchi, or other lumens, of the patient. Following a natural lumen, for example, can allow a surgeon to operate at a work site while making fewer and/or smaller incisions through healthy tissue, although an incision may be needed at locations where the surgical device enters or leaves a natural lumen. Surgical devices that are able to follow a natural lumen or other tortuous path must therefore be flexible so as to permit bending (e.g., curving) and also steerable so as to permit control over such bending. Various surgical applications, particularly those associated with small lumens and/or lumens having tight bends or bifurcations, for example, as encountered in pulmonary and/or neurological applications among others, may require portions of an elongate surgical device to exhibit a relatively small radius of curvature when bending, particularly in order to reach the ultimate work site. In general, depending on the application, various curvatures and degree of curvatures may be desired along a length of the bendable, steerable device.

In some cases, jointed link structures can be disposed at a distal end portion of an elongate surgical instrument (i.e., an end portion of the instrument closest to the work site when the instrument is in use) where controlled steering, bending with small radii of curvature, and/or large and/or multiple DOF motion can be beneficial. Accordingly, a wrist that is formed by a jointed link structure can be provided toward the distal end of an elongate surgical device to support an end effector (e.g., a tool such as a clamp, blade, scissors, cautery member, etc., and combinations thereof). Entry guides (e.g., guide tubes) and/or other similar endoscopic structures that facilitate insertion and removal of surgical instruments and tools, and that facilitate reaching a target work site of a minimally invasive surgical procedure, also can be formed of jointed link structures to provide desired flexibility and bending to enable those devices to traverse and be steered along tortuous paths, such as, for example, body lumens. Entry guides generally contain one or more channels through which other surgical instruments can be inserted and removed. Using an entry guide can also allow instruments to be changed without requiring a delicate steering procedure each time a different instrument is needed.

Aside from the ability to traverse narrow and tortuous paths, the overall size of minimally invasive surgical instruments may pose constraints on the design of such instruments. In general, it is desirable for the overall size, including the outer lateral dimensions (e.g., diameter), of such instruments to be relatively small to fit within narrow lumens and other passages. In some cases, therefore, it is desirable to select the number and placement of force transmission elements so as to reduce the overall size of the jointed link structures. For example, the number and placement of force transmission elements that interconnect a series of articulably coupled links to provide actuation forces to control bending of the structure may be such that the one or more force transmission elements pass through one or more links without directly attaching and terminating at such links. For example, one or more force transmission elements may pass through one or more proximal links ("intermediate" links) of a series of links and ultimately terminate and directly attach to a distal link ("termination" link) of the series, with the intermediate links of the series not having any force transmission elements terminating and directly attaching thereto. Accordingly, the bending and steering of a plurality of joints (or link pairs) in a series is actuated through a single force transmission element (or single set of force transmission elements in the case of multiple bend directions and or DOFs) without each joint or link pair including a termination link and thus being capable of individual direct bending by actuation of a force transmission element directly attached to such a link pair. Such a configuration is sometimes referred to as "underconstrained." In other words, the steering and bending of multiple link pairs is actuated by a single force transmission element or single set of force transmission elements that is attached to and terminates at a link of one of the link pairs in a series of such link pairs. Such "underconstrained" structures, however, can pose challenges in attempting to controllably steer and bend, thereby resulting in unpredictable and/or uncontrollable movement (articulation) of the links.

Controls for such jointed link structures, including underconstrained structures, are sometimes based on a so-called "equal angle assumption," wherein it is assumed that a series of link pairs, for example, that includes intermediate links bounded by a termination link, are bent at roughly the same angle about their respective joints in response to actuation of the one or more force transmission elements directly attached to the termination link. Depending on various forces that may be acting on the links, such as, for example, joint friction, and resistances due to skin and/or payload of the structure, the equal angle assumption may not accurately reflect the actual orientation of link pairs. Moreover, in some cases, particularly when such structures are used in very small lumens and other passages, it may be undesirable to provide a series of interconnected link pairs that all bend at about the same angle since doing so can result in a larger overall bend radius of curvature of the series of link pairs. For a further explanation of jointed link systems that incorporate control systems based on an equal angle assumption, reference is made to U.S. Pat. No. 6,817,974 B2, (filed Jun. 28, 2002; entitled "Surgical Tool Having Positively Positionable Tendon-Actuated Multi-Disk Wrist Joint"), which is incorporated by reference herein in its entirety.

It may be desirable, therefore, to provide a jointed link structure which can be more controllably bent in order to perform a wide range of minimally invasive surgical procedures, including those which require traversal of small, tortuous paths to a work site. It also may be desirable to provide a jointed link structure that can be more controllably bent while the overall dimensions (e.g., including diameter) of the structure is kept relatively small. Moreover, it may be desirable to provide jointed link structures that are relatively robust in design and relatively inexpensive to manufacture, and that can achieve controlled bending through the use of relatively simple mechanical designs.

SUMMARY

The present teachings may solve one or more of the above-mentioned problems and/or may demonstrate one or more of the above-mentioned desirable features. Other features and/or advantages may become apparent from the description that follows.

In accordance with various exemplary embodiments of the present teachings, a surgical device can include a first pair of articulably coupled links, a second pair of articulably coupled links, and a tension member coupled to the first pair of links and the second pair of links such that altering tension in the tension member exerts a force tending to articulate the first pair of links and the second pair of links so as to bend the first pair of links and the second pair of links. The surgical device can be configured such that the first pair of links has a lower resistance to bending than the second pair of links upon altering the tension in the tension member.

In accordance with various exemplary embodiments of the present teachings contemplate a method for controlling movement of a surgical device including a plurality of articulably coupled links connected via a tension member, the device having a first end, a second end, and a longitudinal axis between the first and second end when the structure is in a straight orientation. The method can include altering tension in the tension member to exert a force to articulate the articulably coupled links to place the links in a bent orientation, wherein a first pair of the links resists articulation to the bent orientation less than a second pair of the links in response to altering the tension in the tension member.

Additional objects and advantages of the present teachings will be set forth in part in the description which follows, and in part will be obvious from the description, or may be learned by practice of the invention. At least some of those objects and advantages of the invention will be realized and attained by means of the elements and combinations particularly pointed out in the appended claims.

It is to be understood that both the foregoing general description and the following detailed description are exemplary and explanatory only and are not restrictive of the present teachings and claimed invention.

BRIEF DESCRIPTION OF THE DRAWINGS

The present teachings can be understood from the following detailed description, either alone or together with the accompanying drawings. The drawings are included to provide a further understanding of the present teachings, and are incorporated in and constitute a part of this specification. The drawings illustrate one or more exemplary embodiments of the present teachings and together with the description serve to explain certain principles and operation. In the drawings.

DETAILED DESCRIPTION OF VARIOUS EXEMPLARY EMBODIMENTS

This description and the accompanying drawings that illustrate exemplary embodiments should not be taken as limiting, with the claims defining the scope of the present teachings. Various mechanical, compositional, structural, electrical, and operational changes may be made without departing from the scope of this description and the invention as claimed, including equivalents. In some instances, well-known structures, and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Figure 10:
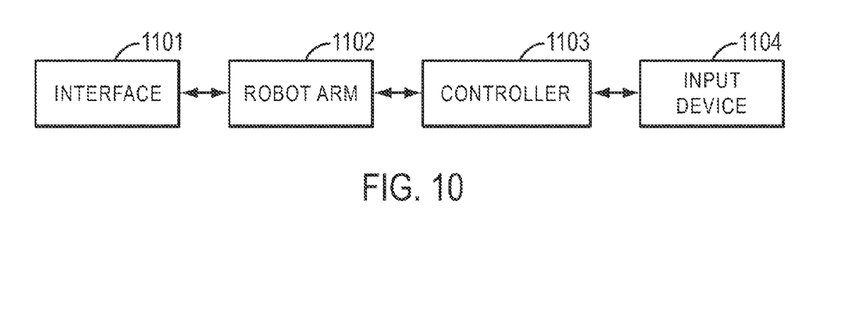
FIG. 10 is a block diagram of a teleoperation portion of a robotic surgical system using a jointed link structure in accordance with an exemplary embodiment of the present teachings.

Exemplary embodiments described herein include various minimally invasive surgical devices, which may, for example, be used in conjunction with various robotic surgical systems. Robotic surgical systems are known, and examples of certain telerobotic surgical features and components may be found in systems such as the da Vinci® Surgical System (specifically, a Model IS3000, marketed as the da Vinci® Si™ HD™ Surgical System), commercialized by Intuitive Surgical, Inc. of Sunnyvale, Calif. For example, with reference to FIG. 10 showing a block diagram for a teleoperation portion of a robotic surgical system, in an exemplary embodiment, a jointed link structure in accordance with the present teachings can be operated via an electromechanical interface 1101 which electrically and mechanically couples the jointed link structure to a robot arm 1102. The movement of the robot arm 1102 is controlled by a controller 1103 in response to operator manipulation of an input device 1104. Either or both the interface 1101 and the robot arm 1102 include motors that drive the cables used to steer the jointed link structure. In addition to controlling bending of the jointed link structure, the robot arm 1102 may also be configured to insert/retract the jointed link structure into and out of an aperture (e.g., natural orifice or minimally invasive incision) in the patient, rotate the jointed link structure about its central axis, and/or rotate the electromechanical interface 1101 about a pivot point at the aperture. The controller 1103 can be implemented as hardware, firmware or software (or a combination thereof) in the one or more computers along with the processors (not shown). In an alternative exemplary embodiment, the jointed link structures in accordance with the present teachings can be operated manually by an operator and in such cases, for example, a handle can serve as the mechanical and/or electrical interface with appropriate levers or other control mechanism(s) for controllably orienting and steering the jointed link structure. As those have ordinary skill in the art would be familiar with, the orientation and steering of the jointed link structure can occur by manipulating control mechanisms on the handle that actuate force transmission elements (e.g., pull cables) coupled with the jointed link structure. Thus, as is explained further below, whether used in conjunction with a telerobotic system or a manually operated system, the jointed link structures may be mechanically and/or electrically coupled to a backend actuation system to exert forces on the structure, including the force transmission elements, for steering and orienting the structure.

As used herein, the term "bendable" and "flexible" and variations thereof in association with a mechanical structure, such as, for example, a jointed link structure, should be broadly construed. The terms describe a structure that can be repeatedly bent (e.g., into various curved patterns) and restored to its original shape without permanent deformation and/or other damage to the structure. As those of ordinary skill in the art would understand, many "rigid" structures have a slight inherent resilient "bendiness" or flexibility due to material properties, although such structures are not considered bendable or flexible as the terms are used herein.

As used herein, the term "termination link" and variations thereof can refer to links to which one or more force transmission elements are directly attached and at which the one or more force transmission elements terminate. In various exemplary embodiments herein, wherein force transmission elements have proximal ends connecting to a proximally disposed backend mechanism and extend from the backend mechanism through a series of links to ultimately attach to and terminate at a distal link of the series, such distal link is a termination link. In various exemplary embodiments, a force transmission element may terminate and attach at an end of the force transmission element (i.e., the end opposite to the end that attaches to a backend mechanism). In various alternative exemplary embodiments, a force transmission element may attach and terminate at a termination link by being routed in a recirculating, folded configuration (e.g., a loop or U-shaped configuration) so as to attach and terminate at a link at the folded portion of the force transmission element, with the two ends of the force transmission element being attached at locations, such as a backend mechanism, of the structure. This alternative configuration permits an actuation force on the force transmission element to result in a greater (e.g., double) change in force transmission path length. Reference is made to U.S. Pat. No. 6,817,974 B2, incorporated by reference herein, for exemplary embodiments of a jointed link structure showing cables that fold over at the links where they terminate. Those having ordinary skill in the art are familiar with force transmission elements being routed in both ways to ultimately attach and terminate at a termination link. Also, it should be understood that the attachment of a force transmission element need not be a direct, contacting attachment, but can occur through another element to fixedly attach the force transmission element to the link, such as, for example, via a pulley or other coupling as those of ordinary skill in the art are familiar with. As described below, the series of proximal links in this example through which the one or more force transmission elements pass but no force transmission elements are directly, fixedly attached are considered "intermediate links." In this way, an actuation force transferred via the one or more force transmission elements directly exerts a force, for example, at its termination location and to the termination link to articulate and bend the structure. A sufficient actuation force transmitted by a force transmission element, can cause a termination link and/or link pair to directly move and articulate about a joint associated with the link and/or link pair.

As used herein, the terms "intermediate link," "intermediate link pairs," and variations thereof can refer to links or link pairs through which one or more force transmission elements pass, for example through force transmission element routing channels, but do not directly connect to or terminate at such links or link pairs.

As discussed above, various robotically controlled and/or other minimally invasive surgical procedures employ a variety of jointed link structures to provide controlled steering and bending of surgical instruments, for example, either to traverse through relatively small, tortuous passages (e.g., lumens) to reach a target work site and/or to accurately position an end effector or other tool while performing a procedure at the work site. Exemplary jointed link structures in accordance with present teachings can include, among others, arms for surgical instruments, entry guides (e.g., endoscopic structures) to introduce other flexible surgical instruments, and/or wrists that support and position end effectors at distal ends of surgical instruments. Such devices can include a single, continuous articulating jointed link structure, or a plurality of such structures separated from one another by interposed rigid segments or other flexible structures, for example.

The present teachings contemplate providing jointed link structures that permit preferential bending to occur at predetermined locations (i.e., at predetermined joints or link pairs) along the length of the structure in response to actuation of force transmission elements used to bend and steer the structure. The present teachings further contemplate embodiments in which preferential bending of a jointed link structure can be accomplished without relying on individually controlling and actuating each link pair in the structure via an individual force transmission element or set of force transmission elements (e.g., tension members) fixedly attached and terminating at each link in a series of links making up the jointed link structure. Providing jointed link structures that exhibit preferential bending in accordance with exemplary embodiments of the present teachings can permit a wide range of surgical applications to be performed using devices having reduced outer dimensions (e.g., diameters).

Various exemplary embodiments of the present teachings provide steerable elongate surgical instruments that are formed of a plurality of links connected in series wherein adjacent links (link pairs) are articulably coupled to each other via respective joints so as to form a jointed link structure. The links in a link pair are configured to be articulated relative to each other about the joint to provide overall bending of the elongate structure. According to various exemplary embodiments, overall bending and steering of the jointed link structure can be controlled by providing jointed link pairs of the structure having differing resistances to bending. In this way, the jointed link structure can exhibit preferential and more controlled bending in response to an actuation force exerted by one or more force transmission elements.

In various exemplary embodiments, a jointed link structure can include a first pair of links that is less resistant to bending than a second pair of links disposed proximally to the first pair of links. Such an arrangement may be desirable, for example, when navigating relatively small and/or complex tortuous paths to a work site so as to achieve bending to a relatively large degree at a more distal end portion of an instrument without a corresponding large translational movement and/or without an overall large radius of curvature of the structure resulting. Such navigation can be encountered, for example, in the bronchi of the lungs and other small and complex lumens. In other applications, however, it may be desirable to provide a relatively large degree of bending at a location proximal to the distal end portion of the structure. This may enable a device to work around a curved path while permitting fine motions of one or more distal link pairs that extend from the proximally bent link pair(s). A jointed link structure that can preferentially bend proximally also can be desirable for applications for which relatively large translational motions are desired with minimal changes in orientation at a distal end portion, for example, when working on a large planar surface (e.g., as encountered when placing diaphragmatic pacing leads).

Thus, in some circumstances, preferentially bending a link pair at the tip or distal end portion of a jointed link structure, for example, as compared to a link pair proximal to the tip or distal end portion, can enable the surgical instrument to reach a work site that otherwise may be inaccessible. For example, preferentially bending the tip or distal end portion can reduce the overall radius of curvature of a series of interconnected links, including links defining the tip or distal end portion, during bending. Likewise, preferentially bending a proximal portion of a jointed link structure as compared to a distal portion of the jointed link structure can enlarge the workspace while minimizing changes in orientation. Thus, various exemplary embodiments of the present teachings the employ preferential bending of jointed link structures may increase the number and/or locations of target work sites that a minimally invasive and/or robotically controlled surgical instrument can reach.

In accordance with various exemplary embodiments, preferential bending may be achieved in jointed link structures which use force transmission elements (e.g., cables and/or other tension members) to exert a steering actuation force on the structure. In particular, exemplary embodiments of the present teachings provide jointed link structures that are "underconstrained" in that each joint (i.e., link pair) in the structure is not individually actuatable and actively articulated by force transmission elements, but can nonetheless be more controllably steered and preferentially bent by configuring the joints to exhibit desired relative resistance to (or relative preference for) bending of the link pair articulably coupled via the joint.

Although the exemplary embodiments illustrated in the figures and described below are discussed in the context of a jointed link structure that is configured as a flexible surgical instrument for reaching a target work site to perform a minimally invasive surgical procedure, it should be understood that the principles of the present teachings can be applied to a variety of other types of jointed link structures that form all or part of surgical and/or non-surgical instruments.

Figure 1A:
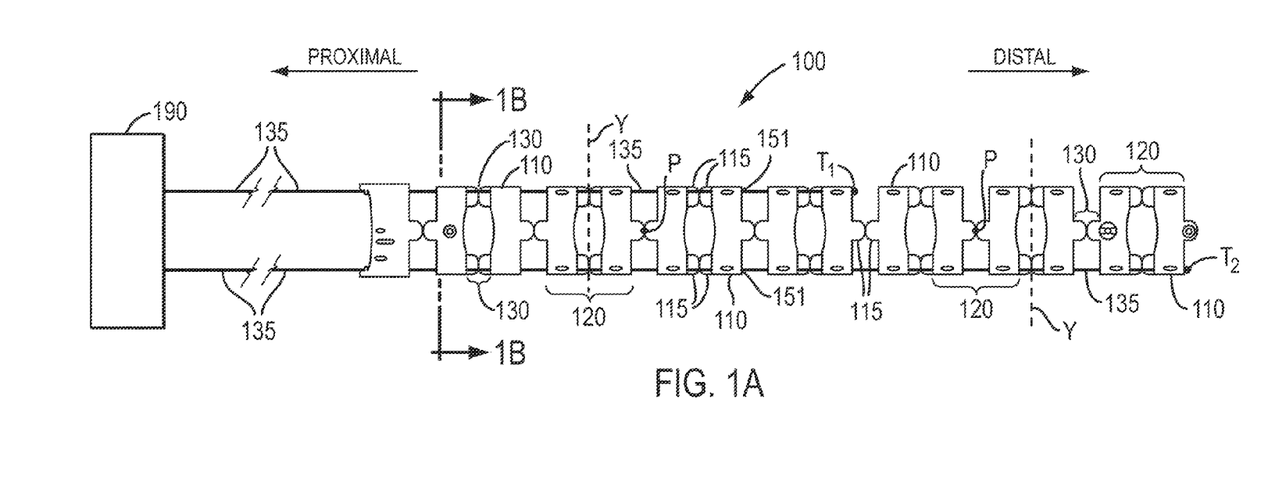
FIG. 1A is a diagrammatic, perspective view of an exemplary embodiment of a steerable jointed link structure.

With reference to FIG. 1A, an exemplary embodiment of a jointed link structure 100 having an elongated configuration is illustrated. Those having ordinary skill in the art would appreciate that the structure 100 shown can include many more links or fewer links than are shown in the figure or can include multiple jointed link structures 100 connected to one another via rigid or non-rigid segments therebetween. FIG. 1A, therefore, is intended to provide a simplified, diagrammatic representation of a jointed link structure. In various nonlimiting exemplary embodiments, the jointed link structure 100 may be a flexible, steerable arm (which could in exemplary embodiments include two to five joints (link pairs) for each degree of freedom, for example, the jointed link structure may include four to ten joints (link pairs) for a structure configured to produce both yaw and pitch movement. The jointed link structure 100 can thus serve as a flexible, steerable device that can bend as desired to various curved patterns in order to follow a narrow, tortuous path. In an exemplary embodiment, the structure 100 can have a generally tubular configuration so as to serve as an entry guide (or guide tube) via which various other surgical instruments can be introduced and advanced to a work site during a minimally invasive surgical procedure. However, as is explained further below, use of the structure as an entry guide is not limiting and a variety of uses for such a structure, such as, for example, as various flexible, steerable arms and wrists are also envisioned. In various exemplary embodiments, the outer diameter of the structure 100 ranges from about 3 mm to about 25 mm, for example, the diameter may be about 18 mm to about 22 mm, particularly when used as a guide tube. The overall length of the structure 100 may be selected according to the types of procedures being performed, however, in various exemplary embodiments, the length may be at least about 60 cm or more, for example 100 cm or more.

The structure 100 includes a plurality of interconnected rigid links 110 (only a few of which are labeled in FIG. 1A) arranged in series from a proximal end to a distal end from the perspective as labeled in FIG. 1A. Consecutive links 110 articulate relative to each other via joints 130 disposed therebetween, with each link-joint-link combination defining a link pair 120 (a few of which are labeled in FIG. 1A). As in the exemplary embodiment of FIG. 1A, if each consecutive link in a series of links is separated by a joint, consecutive link pairs can share a common link. In the exemplary embodiment of FIG. 1A, consecutive joints 130 are provided so as to provide articulation of consecutive link pairs 120 about orthogonally disposed axes. The joints 130 visible in the FIG. 1A are configured to permit articulation of the respective link pairs 120 incorporating those joints 130 about an axis "P" into the plane of the drawing sheet, whereas the joints 130 not visible in the figure are configured to permit articulation of respective joint pairs 120 about an axis "Y" shown. In this way, as those having ordinary skill in the art are familiar with, both "pitch" and "yaw" joints are provided and corresponding pitch and yaw movement of the structure 100 can be implemented. It should be understood, however, that the present teachings also encompass structures that permit single DOF motion and all the joints could be configured to provide pivoting of adjacent links about parallel axes.

In the exemplary embodiment of FIG. 1A, two generally convex protrusions 115 disposed substantially diametrically opposite each other are provided on the opposing axial faces of each link 110. The surfaces of the protrusions 115 on adjacent links 110 are placed in rolling contact with each other to create the joints 130 about which the link pairs 120 pivot via rolling the contact surfaces of the protrusions 115 along each other. Other exemplary embodiments of rolling joint configurations which could be used to form the joints 130 are disclosed in U.S. Pat. No. 6,817,974 B2 (filed Jun. 28, 2002, entitled "Surgical Tool Having Positively Positionable Tendon-Actuated Multi-Disk Wrist Joint"), incorporated by reference herein; and U.S. Application Publication No. US 2005/0273084 A1 (filed Aug. 26, 2004, entitled "Link Systems and Articulation Mechanisms for Remote Manipulation of Surgical or Diagnostic Tools"), which is incorporated by reference herein in its entirety.

Figure 1B:
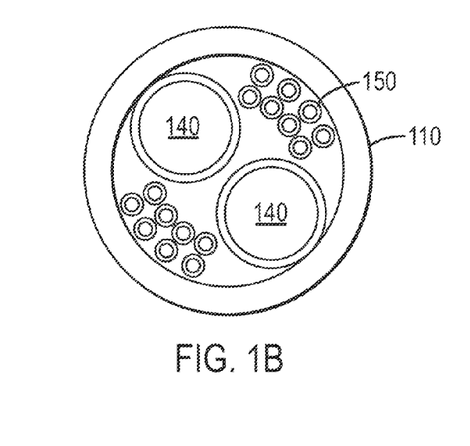
FIG. 1B is a cross-sectional view of a link taken from the perspective 1B-1B in the exemplary embodiment of FIG. 1A.

As shown in the cross-sectional view of FIG. 1B, in an exemplary embodiment, the links 110 may be substantially rigid structures having a generally circular or rounded cross-section. In various exemplary embodiments, the links 110 can be made from a metal or alloy, such as, for example, stainless steel or aluminum, or from polymers, such as for example, polyether ether ketone (PEEK), or other biocompatible materials typically used for surgical devices, and combinations thereof.

Figure 2:
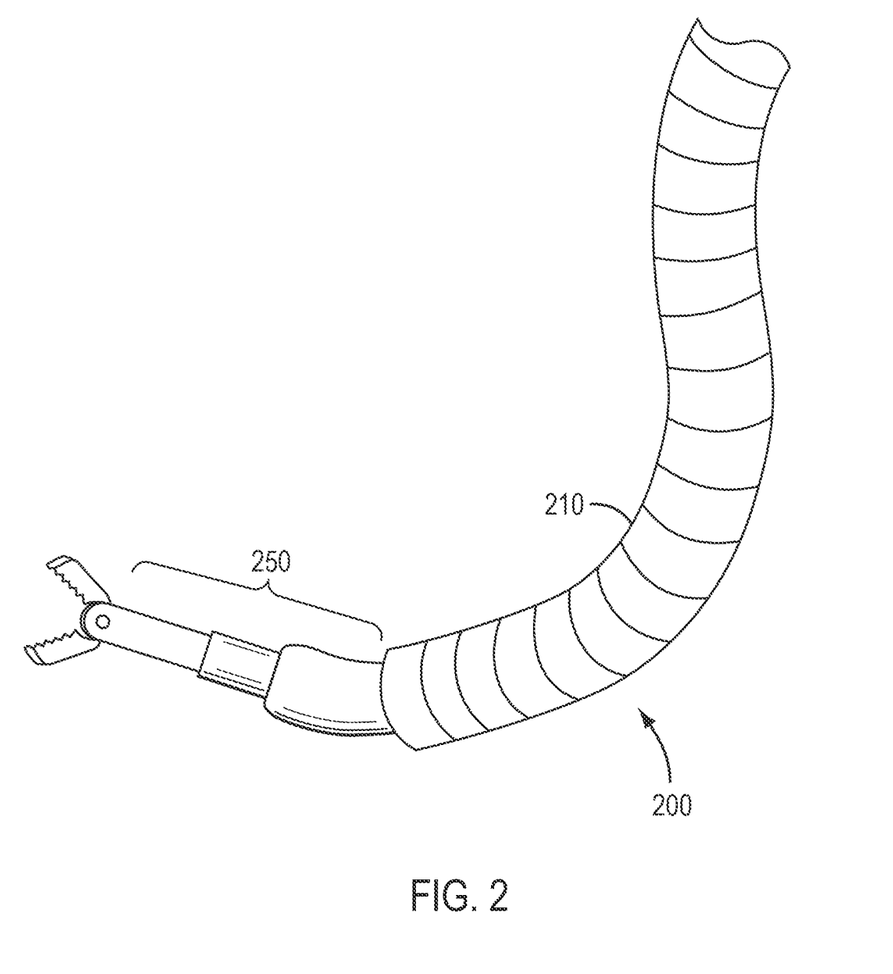
FIG. 2 is a schematic, partial perspective view of an exemplary embodiment of a jointed link guide tube with a surgical instrument received in the guide tube.

As shown in FIG. 1B, in an exemplary embodiment, such as when the structure 100 is a guide tube, the links 100 can define one or more relatively larger instrument channels 140 (two being illustrated in the exemplary embodiment of FIG. 1B) for example, for guiding and/or housing flexible surgical instruments for use during surgical procedures. The channels 140 can run the majority of the length of the jointed link structure 100 so that, when needed, surgical instruments can be inserted into an opening of a respective channel 140 at a proximal end of the structure 100 and advanced through the channel 140 to eventually emerge at an opening at the distal end of the structure 100. In this way, surgical instruments, including but not limited to, for example, scissors, cauterizing elements, clamps, graspers, scalpels, needles, forceps, sensors, cameras, etc., and/or combinations thereof, can be delivered to the target work site via the one or more channels 140 without having to perform delicate steering operations for each instrument that is inserted. In various exemplary embodiments, the one or more instrument channels may have an internal diameter ranging from about 1 mm to about 8 mm. FIG. 2 illustrates a partial, schematic view of an exemplary embodiment of a guide tube 200 formed of a jointed link structure, in use for guiding a surgical instrument having end effector 250 inserted therethrough. The links 210 of the guide tube 200 in FIG. 2 are shown schematically as a series of disk-like segments for simplicity.

In cases in which a jointed link structure is used as a wrist or an arm, rather than a guide tube, the links may not include instrument channels like 140 shown in FIG. 1B, and/or the channels running along the central portions of the structure may be smaller and need not be configured to receive other instruments.

Also shown in the cross-sectional view of FIG. 1B are a plurality of force transmission element routing channels 150 configured to receive force transmission elements that pass through and interconnect the links 110. The number of routing channels 150 depicted in FIG. 1B is exemplary only and may vary depending on the number of force transmission elements used to control the steering of the system, as is described in further detail below. As shown in FIG. 1B, force transmission elements can be run through routing channels 150 generally disposed toward an outer circumferential region circumscribed by the inner surface of the links 110. The force transmission element routing channels 150 define openings (generally labeled 151 in FIG. 1A) on each face of the links 110 that define force transmission element emergence locations.

Passing through (via the routing channels 150) and connecting the links 110 are force transmission elements 135. For ease of illustration, only 2 force transmission elements 135 are illustrated in FIG. 1A, one of which is shown terminating and attached to a link 110 at T1 and the other of which is shown terminating and attached to a link 110 at T2. Where they terminate, force transmission elements 135 may be attached to the links 110 via a variety of attachment mechanisms with which those having ordinary skill in the art are familiar, including but not limited to, enlarged beads at the end of force transmission elements that prevent passage through the passages 150, knots, welding, pulleys, etc. In the exemplary embodiment of FIG. 1A, the force transmission elements 135 are tension members, such as, for example, stranded or woven cables, monofilaments, tubes, and/or other similar tendon-like structures with sufficient strength and flexibility to exert steering forces on the jointed link structure 100. The force transmission elements 135 can have proximal ends connected to a backend actuation (drive) mechanism shown schematically as 190. The actuation mechanism 190 can in turn be connected to a computer-controlled motor pack (not shown) or the like to exert tensioning forces on the force transmission elements 135 in order to steer the linked structure 100. For example, in a robotically controlled application, a control system may include a user interface operated by a surgeon and a computer executing software can control the motor pack. For exemplary backend actuation mechanisms and control systems that could be used to actuate the force transmission elements 135 to provide steering and articulation control of the structure 100, reference is made to U.S. Patent Application Publication No. US 2010/0331820 A1 (filed Jun. 30, 2009; entitled "Compliant Surgical Device"); U.S. patent application Ser. No. 12/780,417 (filed May 14, 2010; entitled "Drive Force Control in Medical Instrument Providing Position Measurement"); U.S. patent application Ser. No. 12/945,734 (filed Nov. 12, 2010; entitled "Tension Control in Actuation of Multijoint Medical Instrument"); U.S. Patent Application Publication No. US 2006/0052664 A1 (filed Mar. 9, 2006; entitled "Connector Device for a Controllable Instrument"); and U.S. Patent Application Publication No. US 2010/0082041 (filed Sep. 30, 2001; entitled "Passive Preload Capstan Drive For Surgical Instruments"), each of which is incorporated by reference herein. It is envisioned, however, that a variety of actuation methods and techniques known to those skilled in the art can be implemented in various exemplary embodiments of the present teachings to provide actuation forces via force transmission elements (e.g., tension members) to cause articulation and steering of the jointed link structures.

Those having ordinary skill in the art would appreciate that backend interfaces and the like (not shown) also may be in mechanical and/or electrical communication with the structure 100, as illustrated in FIG. 1A, or systems coupled thereto to provide remote operation of the same during various surgical procedures.

As mentioned above, in various exemplary embodiments, to reduce the size of the overall structure 100, it may be desirable to reduce the number of force transmission elements used to articulate and steer the structure 100. In other words, rather than attaching a force transmission element or set of force transmission elements 135 to each distal link 100 of a link pair 120 to individually actuate each joint 130 (i.e., individually articulate each link pair 120), fewer force transmission elements 135 are used and the jointed link structure 100 may be underconstrained in that some link pairs 120 may not include a termination link 110 that is directly attached to and actuated by one or more force transmission elements 135. Rather, the movement (articulation about their incorporated joint 130) of such "intermediate" link pairs 120 is generally responsive to movement of a more distal termination link pair 120 to which a force transmission element 135 is directly, fixedly attached and terminated to directly actuate movement thereof. As mentioned above, in the exemplary embodiment of FIG. 1A, two of the links 110 are termination links (respectively associated with the force transmission elements 135 terminating at $T_1$ and $T_2$) and the structure 100 is underconstrained.

Figure 3A:
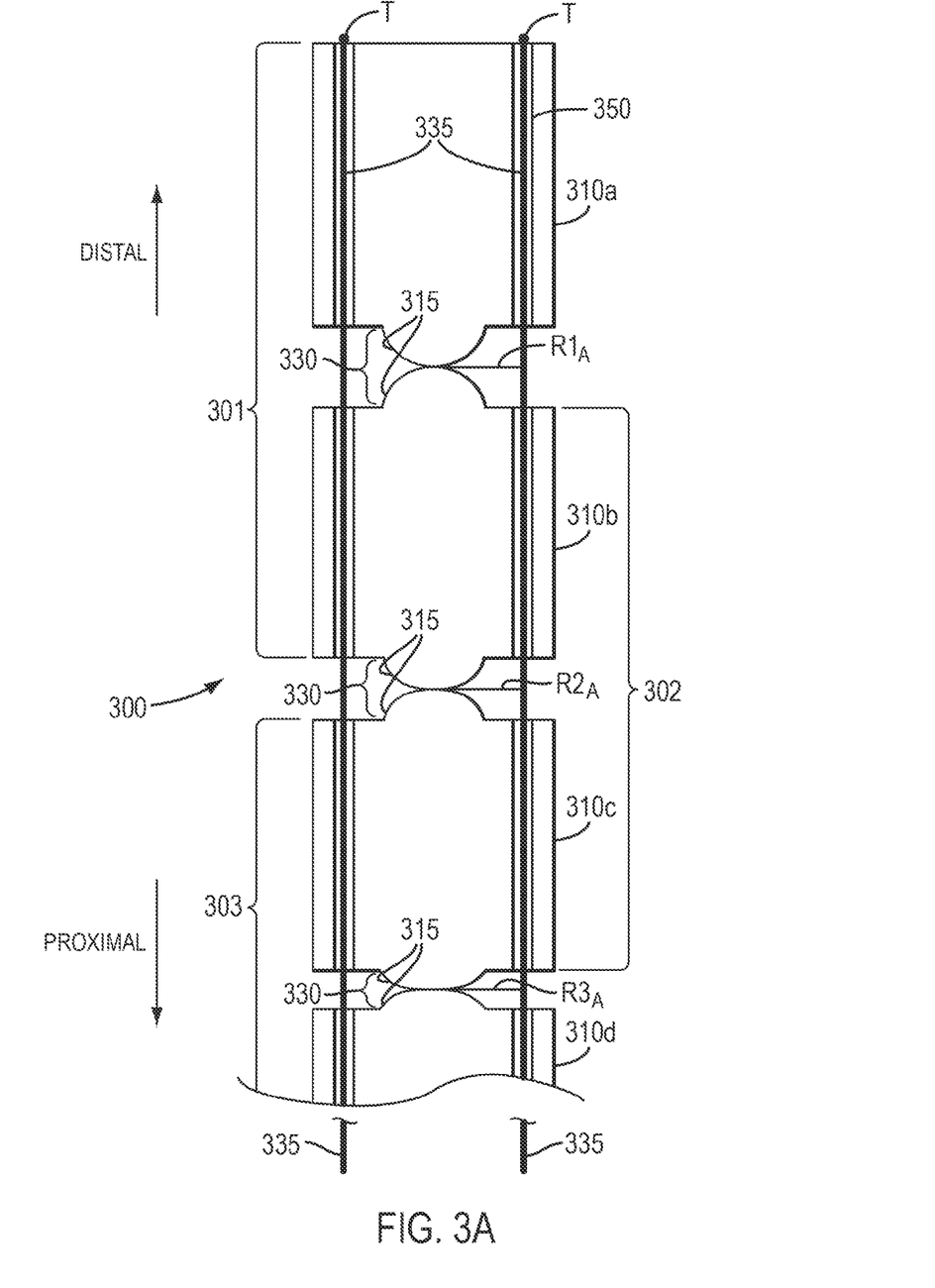
FIG. 3A is a schematic, partial sectional view of an exemplary embodiment of a series of jointed link pairs in a straight orientation that exhibit preferential bending in accordance with the present teachings.

FIG. 3A shows a schematic partial sectional view of an exemplary embodiment of a jointed link structure 300 that enables preferential bending of link pairs at predetermined locations along the structure 300, as will be explained below, which can be utilized as part of the overall structure 100 in FIG. 1A. The exemplary embodiment of FIG. 3A includes a series of interconnected links 310a-310d articulably coupled via joints 330. The joints 330 are formed by rolling contact between surfaces of opposing convex protrusions 315 on the links 310a-310d of the link pairs 301-303, in a manner similar to that described above with reference to FIG. 1A, with differences explained in further detail below. In the view of FIG. 3A, only one pair of rolling contact protrusions 315 forming each joint 330 is depicted as the other pair would be positioned diametrically opposite and thus not shown in the view FIG. 3A (e.g., with reference to FIG. 1A, the protrusions 130 that can be seen in the side view of that structure block similar protrusions that are behind the visible protrusions 130 in the view shown).

The tension members 335 and tension member routing channels 350 also are depicted. However, for simplicity, only one set of two tension members 335 are depicted, but other tension members may be associated with the structure 300 to provide actuation forces for articulating and steering the same, the number of tension members 335 being selected and arranged depending, for example, on the degrees of freedom of articulation of a series of links. The tension members 335 can be attached at their proximal ends to a backend actuation control system (not shown) to exert actuation forces (e.g., control tension) in the tension members 335, for example, as described above with reference to FIG. 1A.

The exemplary configuration of links and joints depicted in FIG. 3A enables preferential bending of the structure 300 without direct, individual actuation of each link pair 301, 302, and 303 shown in FIG. 3A by force transmission elements 335. In other words, in the exemplary embodiment of FIG. 3A, the link pair 301 is closer to a distal end of the structure 300, with force transmission elements 335 directly attached and terminating at link 310a at the locations T such that link 310a is a termination link. The links 310b-310d of link pairs 302 and 303, which are proximal to link pair 301, are intermediate link pairs in that the tension members 335 pass through link pairs 302 and 303 without fixedly attaching to and terminating at links 310b, 310c or 310d. And thus movement (articulation) of the link pairs 302 and 303 is generally in response to direct actuation and movement (articulation) of the link 310 a of link pair 301.

As illustrated in FIG. 3A, the protrusions 315 of the respective joints 330 associated with each link pair 301, 302 and 303 have differing configurations. More specifically, the protrusions 315 of the link pair 301 have a generally hemispherical profile, and the protrusions 315 of the link pair 302 have a flatter profile than the protrusions 315 of the link pair 301. The protrusions 315 of the link pair 303 have an even flatter profile than those of the link pair 302. The differing profiles of the protrusions 315 forming the joints 330 of each link pair 301, 302, and 303 provide differing rolling contact surface areas between the protrusions 315 of each link pair. More specifically, in the embodiment shown, the protrusions 315 of the link pair 301 provide the smallest rolling contact surface area and the protrusions 315 of the link pair 303 provide the largest rolling contact surface area. The profiles depicted in FIG. 3A are exemplary and nonlimiting and those having ordinary skill in the art would appreciate that other profiles could be used to accomplish preferential bending of the link pairs 301, 302 and 303 based on the principles explained in more detail below.

The links 310a-310d have substantially the same overall configuration (e.g., outer diameter) and the tension member routing channels 350 substantially align with each other when the link pairs 301, 302 and 303 are in the straight orientation shown in FIG. 3A. By providing the protrusions 315 of each link pair 301-303 with the differing profiles depicted, exertion of tension in one of the tension members 335 creates a moment on the link pairs tending to articulate the link pairs 301-303 and move them from the straight orientation of FIG. 3A to a bent orientation. The moment exerted is roughly proportional to the moment arm defined by distance R between the point of contact of the protrusions 315 about which a respective link pair will pivot as the link pairs articulate and the unsupported span of the tension member 335 extending between the opposing faces of adjacent links of a link pair. As can be seen in FIG. 3A, therefore, the moment acting on each of the link pairs 301, 302, and 303 is proportional to the each of the respective distances $R1_A$, $R2_A$, and $R3_A$, which in the straight orientation of FIG. 3A are substantially equal.

Figure 3B:
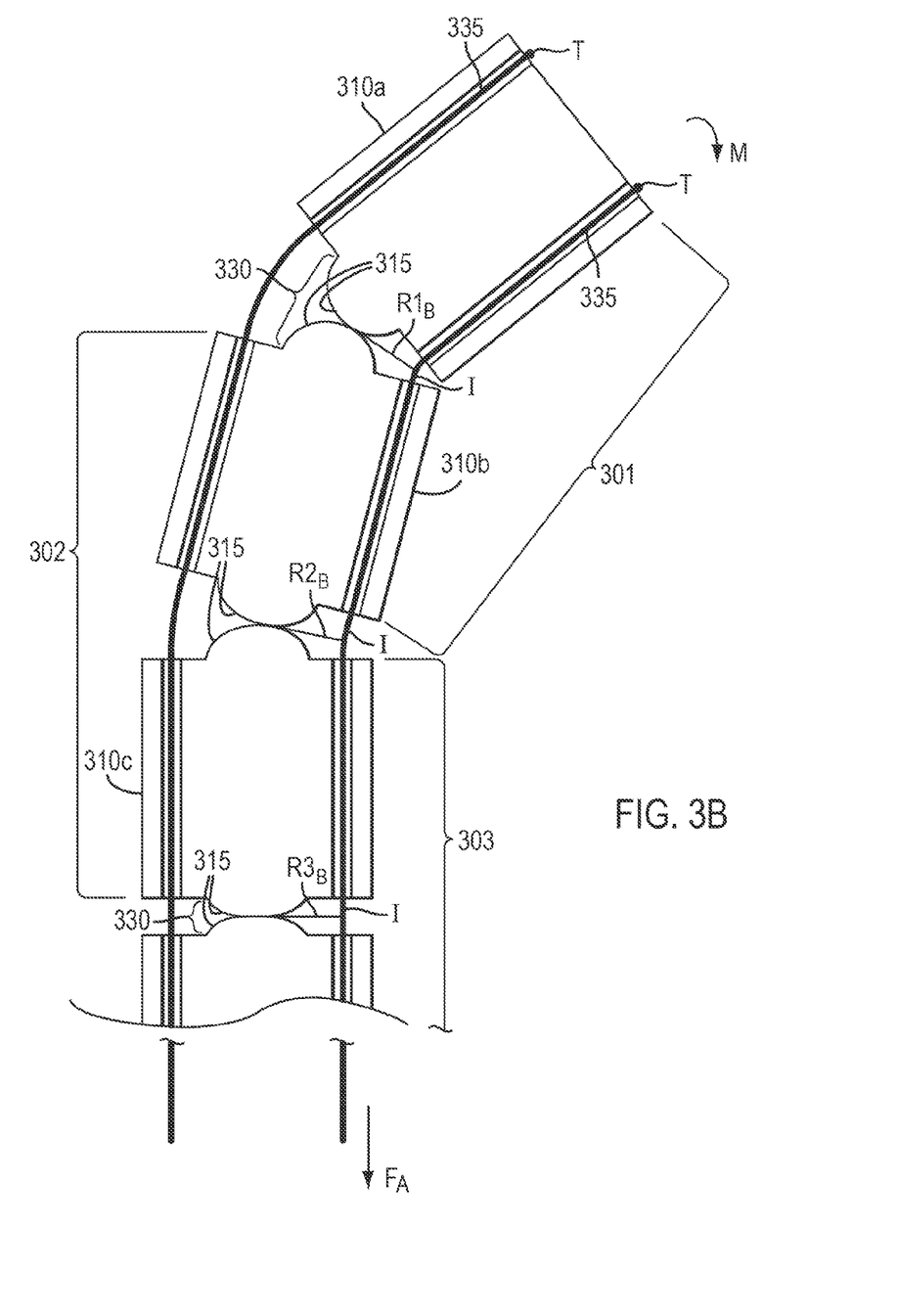
FIG. 3B is schematic. partial sectional view of the exemplary embodiment of FIG. 3A showing link pairs in a bent orientation.

A schematic illustration showing preferential bending in the structure 300 and operation of the structure 300 to accomplish the same is shown in FIG. 3B. As depicted in FIG. 3B, actuating the tension member 335 on the right in the view of FIG. 3B via a pulling force $F_A$, which in various exemplary embodiments can be generated by a backend actuation system (not shown) as described above, creates tension in the tension member 335 on the right in the view of the figure. The fixed attachment of the tension member 335 to the link 310a at termination location T exerts an overall moment M on the structure 300 tending to articulate (in the clockwise direction as viewed in FIG. 3B) the link pairs 301, 302, and 303 about their respective joints 330. However, as the link pairs 301, 302, and 303 begin to articulate about their respective joints 330, the moment arms $R1_B$, $R2_B$, and $R3_B$ differ from each other as a result of the differing profiles of the protrusions 315 forming each joint 330. More specifically, as shown in FIG. 3B, $R1_B$ is greater than $R2_B$ and $R3_B$. Likewise, $R2_B$ is greater than $R3_B$. The different moment arms $R1_B$, $R2_B$, and $R3_B$ corresponding to each link pair 301, 302, and 303 create differing individual moments acting on each link pair 301, 302, and 303, with the moment acting on link pair 301 being the largest and that of link pair 303 being the smallest.

The differing moments acting on the link pairs cause the link pair 301 to articulate and bend in the direction of the applied moment to a greater degree than the link pairs 302 and 303. In other words, the link pair 301 bends to provide a smaller radius of curvature on its inner bend radius (I labeled in FIG. 3B) than the link pairs 302 and 303. In this way, as depicted in FIG. 3B, as actuation and tension (due to $F_A$) in the tension member 335 continues, the link pair 301 may be bent, for example, until reaching or substantially reaching its joint limit. In an exemplary embodiment, the joint limit may be where the opposing axial faces of adjacent links 310a and 310b on an inner bend radius of the link pair 301 come into or close to contact with each other, as illustrated in FIG. 3B. In this position, the link pair 302 disposed just proximal to link pair 301, which has a smaller moment acting on it and consequently a higher resistance to bending than link pair 301, will articulate about its corresponding joint 330 to a degree less than that of the link pair 301. And the link pair 303 will be articulated and bent to an even lesser degree or, for example, substantially not at all at least initially. In the fully bent orientation (i.e., with each of the link pairs 301, 302, and 303 being bent to its respective joint limit like link pair 301 in FIG. 3B), $R1_B > R2_B > R3_B$. This condition will generally be the case throughout exertion of the actuation force to bend the structure 300. Accordingly, the differing link pairs 301, 302, and 303 have differing resistances to bending and preferential bending of the structure 300 at predetermined locations (e.g., at predetermined link pairs) can be achieved.

The differing protrusion profiles of each of the link pairs 301-303 in the exemplary embodiment of FIGS. 3A and 3B, effects a differing change in tension member path length that occurs across each joint 330 of the respective link pairs 301-303 during bending as illustrated in FIG. 3B. That is, in FIGS. 3A and 3B, as compared to the link pairs 302 and 303, the length of the tension member 335 upon which force $F_A$ acts, as measured across the joint 330 of the link pair 301 (e.g., the distance between tension member emergence locations on the opposing faces of the links 310a and 310b) changes (i.e., reduces) by a greater amount as the link pair 301 bends; and likewise for the link pair 302 as compared to the link pair 303. This requires application of a larger bending force for a more proximal joint 330 as compared to a more distal joint 330 in order to change (reduce) the tension member path length across each joint by the same amount. In the exemplary embodiment of FIGS. 3A and 3B, shortening the moment arm $R1_B$ more quickly at the joint 330 corresponding to link pair 301 than the moment arms $R2_B$, $R3_B$ at the joints 330 corresponding to link pairs 302 and 303 encourages the link pair 301 to bend more quickly and for the radius of curvature on the inner bend radius I to be greater than the radii of curvature at link pairs 302 and 303.

In an exemplary embodiment, it may be desirable to configure the link pairs 301-303 such that the link pair 301 reaches its fully bent orientation (e.g., reaches its joint limit) before the link pair 302 begins to articulate to a bent orientation, and likewise for link pairs 302 and 303. In reality, however, this may not be possible to achieve and it is likely that the link pairs 302 and 303 would begin to bend slightly before the link pairs 301 and 302, respectively, having reached their fully bent orientations.

Thus, FIG. 3B demonstrates how the jointed link structure 300 of FIG. 3B can be used to preferentially bend the link pair 301 over the link pairs 302 and 303, and to preferentially bend the link pair 302 over the link pair 303. This can enable the structure 300 to provide a relatively smaller radius of curvature at the distal end portion, including at the joint 330 corresponding to link pair 301, than occurs more proximal to the link pair 301, for example, in link pairs 302 and 303 that include intermediate links 310b-310c.

Although in the exemplary embodiment of FIGS. 3A and 3B, the cable routing channels through the links 310a-310d are substantially aligned in a straight orientation, and the moment arms R1B, R2B and R3B differ as a result of the differing protrusion 315 profiles, those having ordinary skill in the art would understand that modifications to the configurations and arrangements of the joints and/or the cable routing channels can be made while still achieving differing moment arms at each joint and consequent preferential bending of a jointed link structure, and such modifications are considered within the scope of the present teachings.

Figure 4:
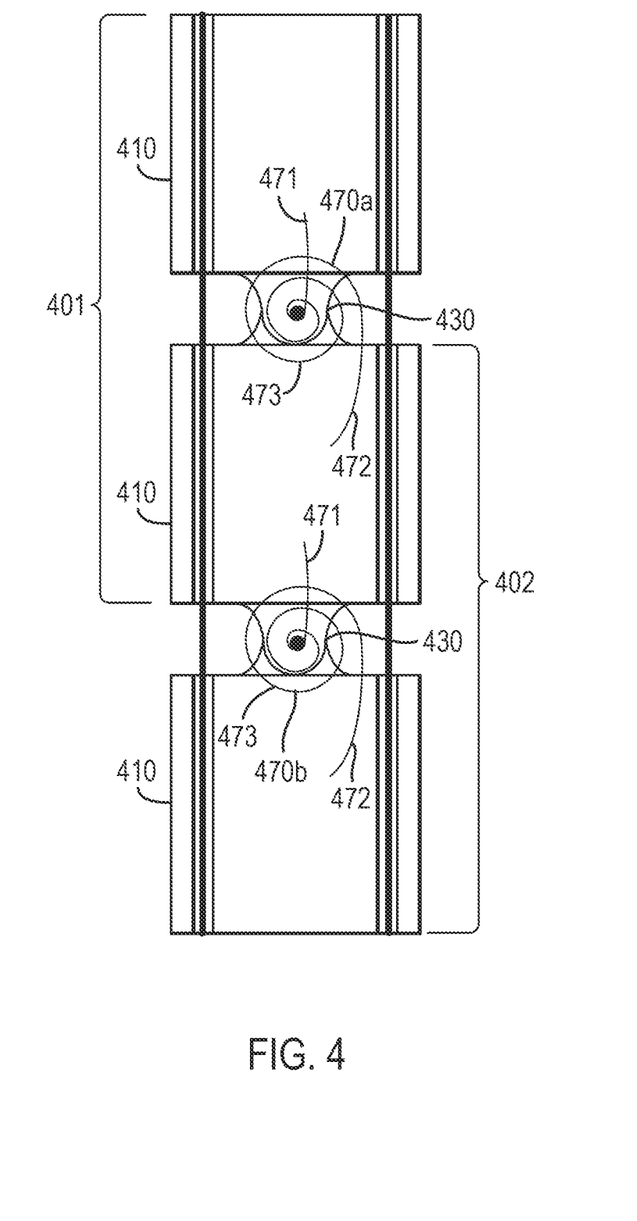
FIGS. 4-8 are schematic, partial sectional views of other exemplary embodiments of a series of jointed link pairs in a straight orientation that exhibit preferential bending in accordance with the present teachings.

Another exemplary embodiment of a jointed link structure configured for preferential bending in accordance with the present teachings is illustrated in FIG. 4. As with FIGS. 3A and 3B, the view of the jointed link structure 400 in FIG. 4 is a partial sectional view showing three links 410 of the structure 400. Similar features that are common to the exemplary embodiment of FIGS. 3A and 3B are not described again here. In the exemplary embodiment of FIG. 4, instead of joints of the link pairs being provided via rolling contact of protrusion surfaces as in the embodiment of FIGS. 3A and 3B, the joints 430 are pin joints. To provide preferential bending, springs 470a and 470b are positioned to connect the respective links 410 in each link pair 401 and 402. In the exemplary embodiment of FIG. 4, the springs 470a, 470b are torsion springs. As shown, the coiled portion 473 of the springs 470a, 470b can be substantially centered about the pin 431 of each pin joint 430 with each of the arms 471 and 472 of the springs connected to a respective link 410 of the link pairs 401 and 402. To provide preferential bending of the link pairs 401 and 402, the springs 470a and 470b can have differing spring constants. For example, the spring 470b corresponding to link pair 402 in the exemplary embodiment of FIG. 4 can have a higher spring constant than the spring 470a corresponding to link pair 401. In this manner, when an actuation force is exerted on a force transmission element, e.g., tension is exerted in one of the tension members 435, due to its higher spring constant, the spring 470b corresponding to link pair 402 will tend to resist bending of the link pair 402 more than will the spring 470a corresponding to the link pair 401. Thus, as with the exemplary embodiment of FIGS. 3A and 3B above, the embodiment of FIG. 4 also permits preferential bending of a series of link pairs that are underconstrained, as has been discussed herein. Although two springs 470a, 470b having differing spring constants are depicted in FIG. 4, it is contemplated that the link pair for which preferential bending over the other link pair is desired can be provided without a spring, while the other link pair for which a higher to resistance to bending is desired can be provided with a spring.

Figure 5:
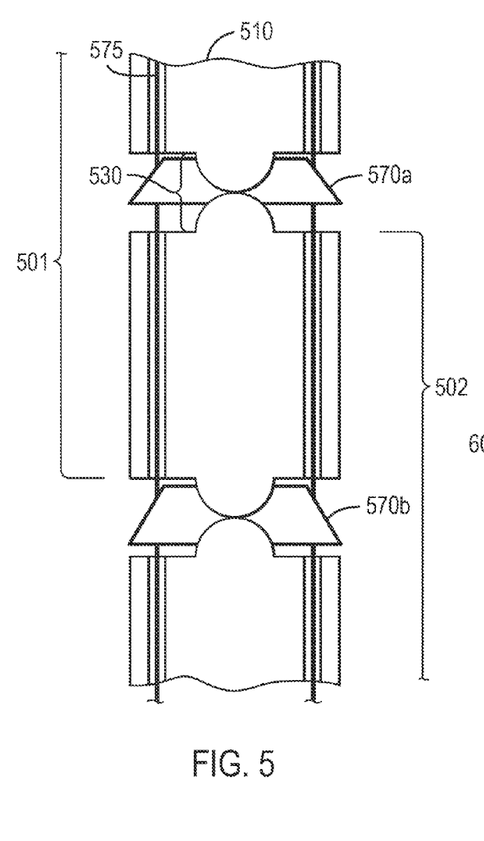

Aside from the torsion spring depicted in FIG. 4, those of ordinary skill in the art would appreciate that a variety of other spring mechanisms could be used and disposed at the joint between links of a link pair to provide a resistance to bending of the link pair. For example, FIG. 5 shows another exemplary embodiment that employs disk springs (e.g., Belleville washers) having differing spring constants disposed at the joints 530 between links 510. As above, the disk spring 570a associated with link pair 501 will provide a greater resistance to bending due to its higher spring constant than will the disk spring 570b associated with link pair 502, in order to result in preferential bending of the link pair 501 over the link pair 502.

Figure 6:
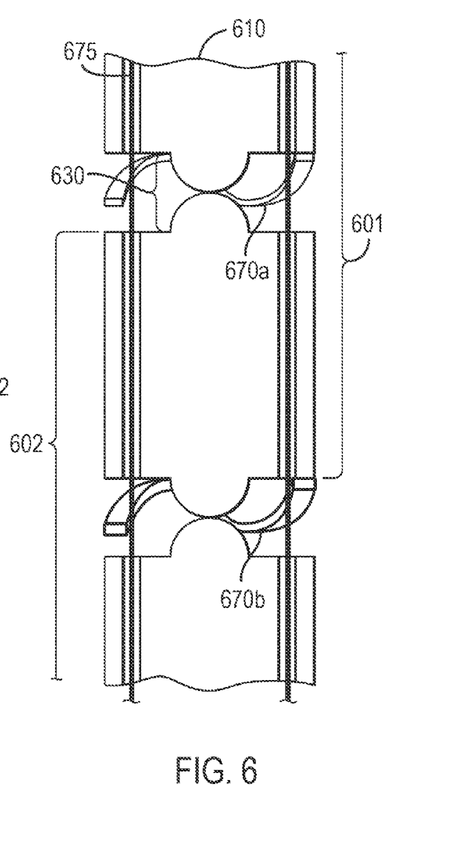

FIG. 6 is similar to FIG. 5 except for the use of wave springs 670a, 670b instead of the disk springs. As with other exemplary embodiments, the wave springs 670a and 670b can have differing spring constants in order to effect preferential bending of the link pairs 601 and 602. For example, the wave spring 670b can have a higher spring constant than wave spring 670a so that the link pair 602 resists bending more than link pair 601. Moreover, based on the generally asymmetrical configuration of the wave springs 670a and 670b, the bending exhibited about the longitudinal axis of the series of links 610 (i.e., clockwise and counterclockwise) may differ from each other. In this way, the bending of the structure is asymmetrical about the longitudinal axis and a greater or lesser degree of bending of the link pairs can be achieved in one direction over the other depending on the selected configuration and arrangement of the wave springs.

Figure 7:
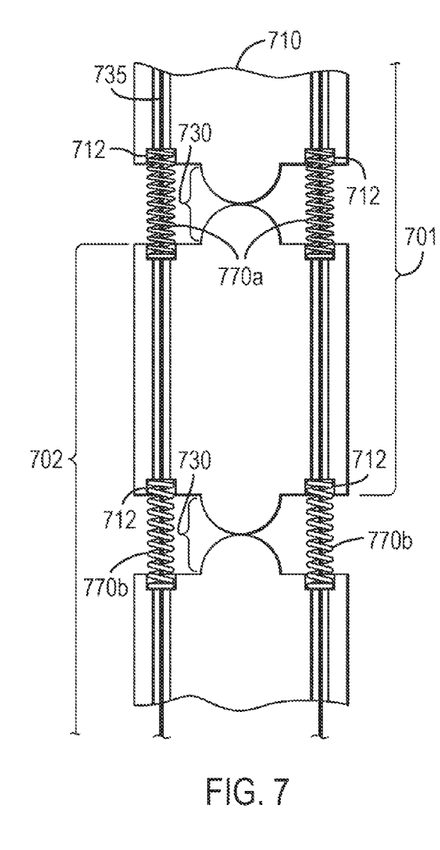

FIG. 7 illustrates an exemplary embodiment using linear springs 770a, 770b connected between the opposing faces of the links 710 of link pairs 701, 702, and situated around the joints 730 of the link pairs 701, 702. As illustrated, in an exemplary embodiment, the tension members 735 can be routed through the springs 770a and 770b. The opposing faces of the links 710 can include recesses 712 configured to receive the springs 770a, 770b, for example, and to retain the springs relative to the links 710. Other mechanisms can also be used to secure the springs 770a, 770b to the links 710, such as for example, welding the springs to the links. In the exemplary embodiment shown, the linear springs 770a and the linear springs 770b can have differing spring constants. For example, the springs 770b can have higher spring constants than the springs 770a such that the link pair 702 has a higher resistance to bending than the link pair 701. Therefore, link pair 701 can preferentially bend compared to the link pair 702 upon actuation of the tension members 735 to bend the series of links 710.

Figure 8:
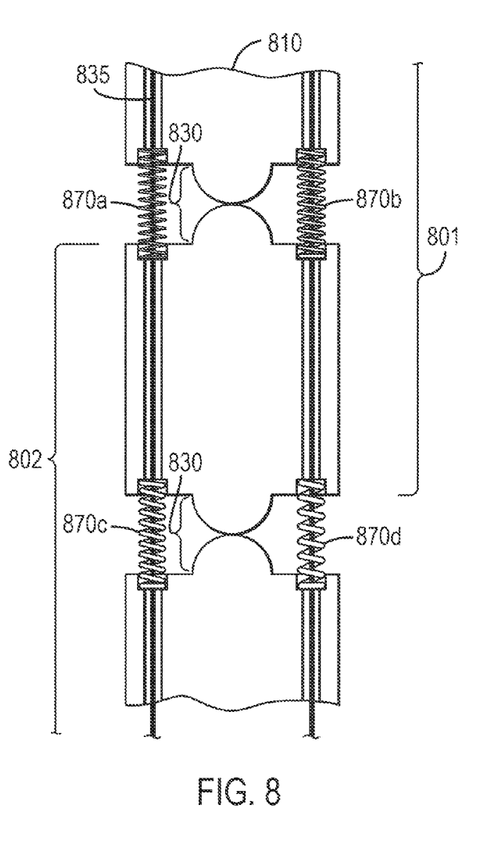

In the exemplary embodiment of FIG. 7 described above, it is contemplated that the resistances to bending resulting from the springs 770a, 770b about the joints 730 are substantially symmetrical about the two bending directions shown in those embodiments (i.e., clockwise and counterclockwise in the perspective of the figures). However, the present teachings also contemplate exemplary embodiments that provide for asymmetrical resistances. The schematic exemplary embodiment of FIG. 8 depicts the use of linear springs 870a-870d (like described above with reference to FIG. 7), wherein each of the four springs 870a-870d shown has a differing spring constant. In this way preferential bending of one joint over the other may occur, as described herein, and also asymmetrical bending in each link pair 801, 802 may occur depending on the direction of bend. For example, the spring constant of 870d may be higher than 870c, and the spring constant of 870b may be higher than 870a. In such a configuration, the link pairs 801 and 802 have a higher resistance to bending in the clockwise direction of FIG. 8 than in the counterclockwise direction. Moreover, as with other exemplary embodiments, the spring constants of 870c and 870d can be higher than the spring constants of 870a and 870b, respectively, to result in a preferential bending of the link pair 801 over the link pair 802 regardless of whether the link pairs 801, 802 are bending in the clockwise or counterclockwise direction. Those having ordinary skill in the art would understand how to modify the various embodiments shown and described herein to achieve similar asymmetrical bending about a joint of a link pair.

As described above with reference to the exemplary embodiment of FIGS. 3A and 3B, in the exemplary embodiments of FIGS. 4-8, differing link pairs in the series of links depicted result in a large degree of bending for the same change in cable path length across the joints of the link pairs. That is, in the embodiments shown in FIGS. 4-8 that use springs having higher spring constants in more proximal joints as compared to more distal joints, the distal link pair bends to a greater degree for the same change in cable path length, and a larger bending force is required to change (reduce) the tension member path length by the same amount across a more proximal joint in comparison to a more distal joint.

The exemplary embodiments of FIGS. 3-8 illustrate a series of link pairs of jointed link structures that each articulate about the same axis and accordingly the portions of the structures shown would exhibit a single DOF articulating movement. However, it should be understood that the present teachings are not limited to jointed link structures that have single DOF articulation but can be implemented in structures having multiple DOF articulation, including, e.g., like the structure 100 in FIG. 1A. In such cases, link pairs that articulate about the same axis may be separated from one another by intermediate link pairs that articulate about a different axis. The separated link pairs that articulate about the same axis can still be configured to provide preferential bending of one link pair over the other in accordance with the present teachings and as exemplified in the description of the embodiments of FIGS. 3-8.

Figure 9:
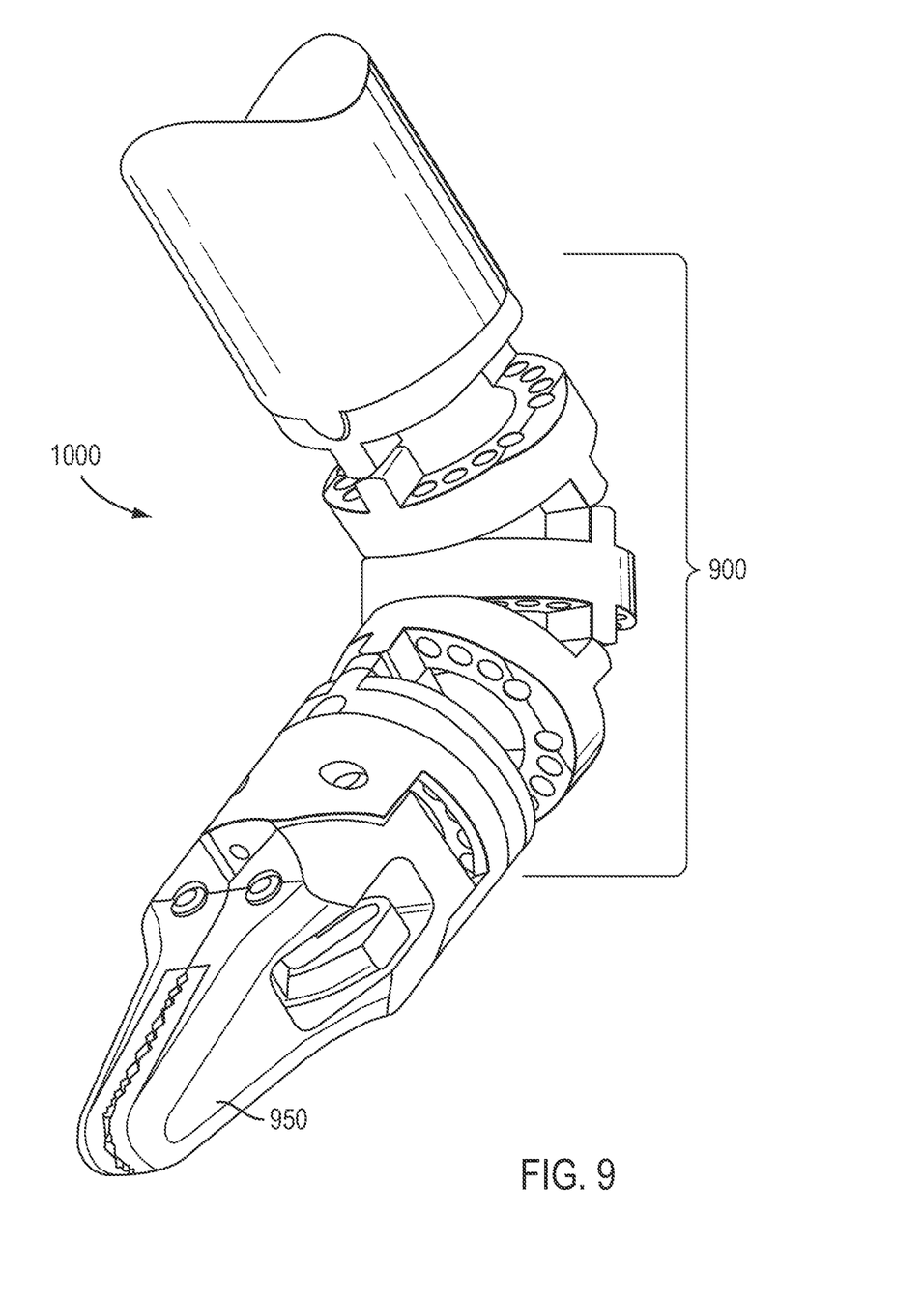
FIG. 9 is a schematic perspective view of another exemplary embodiment of a surgical instrument comprising a wrist supporting an end effector (shown without force transmission elements), wherein the wrist can be formed of a jointed link structure configured for preferential bending in accordance with the present teachings.

As mentioned above, various exemplary embodiments shown and described with reference to FIGS. 1-8 can be used in a guide tube that is formed of one or more jointed link structures exhibiting preferential bending. However, the present teachings should not be considered to be limited to such an embodiment; other devices that employ jointed link structures may be modified to provide preferential bending in accordance with the present teachings. In the context of surgical instruments, for example, the present teachings can apply to wrists and other arms provided as jointed link structures, an exemplary embodiment of the former of which is depicted in FIG. 9 wherein a wrist 900 formed of a jointed link structure is provided at a distal end of an elongate surgical instrument 1000 (only a portion of which is illustrated in FIG. 9 and force transmission elements are not shown) to support and control the positioning of an end effector 950. The wrist 900 is depicted schematically and those of ordinary skill in the art would understand based on the teachings herein how to configure the jointed link structure of the wrist 900 to provide the same with preferential bending. It should be understood that the instrument shown in FIG. 9 is exemplary only and not intended to be limiting of the present teachings as they apply to other wristed surgical instruments having configurations other than that depicted.

Although various exemplary embodiments shown and described herein provide jointed link structures that include a distal link pair that exhibits less resistance to bending (preferential bending) as compared to proximal link pairs, those having ordinary skill in the art will appreciate that modifications to the structures can be made to achieve preferential bending at other predetermined link pair locations along the structure, as desired. For example, link pairs that tend to resist (or prefer) bending as compared to other link pairs can be placed in any desired order and/or location along the structure. Those of ordinary skill in the art would understand based on the present teachings how to modify a variety of jointed link structures to achieve the desired degree and locations of preferential bending along the structure depending, for example, on the application for which the jointed link structure is being used. By way of example only, in the exemplary embodiments of FIGS. 3-8, the placement of the various protrusions or springs can be reversed so as to achieve preferential bending in the proximal link pairs shown over the distal link pairs.

In addition, the exemplary embodiments of jointed link structures, and in particular the configurations of the joints and links, are exemplary only and should not be considered as limiting the present teachings and claims. Numerous existing jointed link structures exist that utilize various configurations for the joints and links in those structures. Those having ordinary skill in the art would appreciate how to modify existing jointed link structures to achieve preferential bending based on the present teachings herein. Nonlimiting examples of suitable architectures of joint and links to form a jointed link structure can be found, for example, in U.S. Pat. No. 6,817,974 B2 (filed Jun. 28, 2002; entitled "Surgical Tool Having Positively Positionable Tendon-Actuated Multi-Disk Wrist Joint"), incorporated by reference herein.

Also, the particular mechanisms described with reference to the exemplary embodiments for achieving preferential bending of jointed link structures, or link pairs with differing resistances to bending, are nonlimiting and exemplary only. Those having ordinary skill in the art would recognize mechanisms other than springs and the contact surface area of rolling protrusions could be employed to provide a relative increase or decrease of a link pair's tendency to bend.

Moreover, applications other than surgical procedures that utilize jointed link structures, as described above, for example, also may benefit from the ability of an elongate structure or portion thereof to preferentially bend so as to be steered along small and/or tortuous paths. Such applications may include, but are not limited to, for example, various types of underconstrained robotic arms, for example, that are used in search and rescue operations through rubble following natural disasters, for exploring between walls to examine wiring, plumbing, insulation, etc., and other similar applications.

Further modifications and alternative embodiments will be apparent to those skilled in the art in view of the disclosure herein. For example, the systems and the methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims.

It is to be understood that the particular examples and embodiments set forth herein are nonlimiting, and modifications to structure, dimensions, materials, and methodologies may be made without departing from the scope of the present teachings.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A surgical device, comprising:
a first pair of articulably coupled links;
a second pair of articulably coupled links; and
a tension member coupled to the first pair of links and the second pair of links, wherein altering tension in the tension member exerts a force tending to articulate the first pair of links and the second pair of links so as to bend the first pair of links and the second pair of links,
wherein the first pair of links comprise opposing link faces having first protrusions in rolling contact with one another wherein in a bent orientation of the first pair of links, the tension member is at a first radial distance from a point of contact between the first protrusions on the opposing link faces of the first pair of links,
wherein the second pair of links comprise opposing link faces having second protrusions in rolling contact with one another wherein in a bent orientation, of the second pair of links, the tension member is at a second radial distance from a point of contact between the second protrusions on the opposing link faces of the second pair of links, and
wherein the first and second radial distances are different.

2. The surgical device of claim 1, wherein the first pair of links is distal to the second pair of links.

3. The surgical device of claim 1, wherein the first pair of links and the second pair of links share a common link.

4. The surgical device of claim 1, wherein the tension member terminates at the distal link of the first pair of links.

5. The surgical device of claim 4, wherein the second pair of links does not include a link at which a tension member terminates.

6. The surgical device of claim 1, wherein the first pair of links is distal to the second pair of links, and wherein the first radial distance is greater than the second radial distance.

7. The surgical device of claim 1, wherein each pair of links comprises a joint articulably coupling the links.

8. The surgical device of claim 1, wherein the first pair of links bends to a greater degree than the second pair of links for the same change in tension member length spanning between opposing faces of respective links of each of the first pair of links and the second pair of links.

9. A method for controlling movement of a surgical device comprising a plurality of articulably coupled links connected via a tension member, the device having a first end, a second end, and a longitudinal axis between the first and second end when the structure is in a straight orientation, the method comprising:

altering tension in the tension member to exert a force to articulate the articulably coupled links to place the links in a bent orientation, wherein a first pair of links comprises opposing link faces having first protrusions in rolling contact with one another wherein in a bent orientation of the first pair of links, the tension member is at a first radial distance from a point of contact between the first protrusions on the opposing link faces of the first pair of links, wherein a second pair of links comprises opposing link faces having second protrusions in rolling contact with one another wherein in a bent orientation, of the second pair of links, the tension member is at a second radial distance from a point of contact between the second protrusions on the opposing link faces of the second pair of links, and wherein the first and second radial distances are different.

10. The method of claim 9, wherein the first pair of links is distal to the second pair of links, and wherein the method comprises articulating the first pair of links to bend the first pair of links by a larger amount than the second pair of links in response to altering the tension in the tension member.

11. The method of claim 9, wherein altering tension in the tension member comprises altering tension in a tension member that passes through at least one link of the plurality of articulably coupled links and terminates and directly attaches to another link distal to the at least one link, and wherein movement of the at least one link is not individually actuatable.

12. The method of claim 9, wherein altering the tension in the tension member alters a length of the tension member spanning between respective links of the first and second link pairs, and wherein the first pair of links bends by a greater amount than the second pair of links in response to altering the length of the tension member between the respective links by the same amount.

* * * * *